(12) United States Patent
Schmaus et al.

(10) Patent No.: US 8,647,651 B2
(45) Date of Patent: Feb. 11, 2014

(54) SYNERGISTIC MIXTURES OF C6- TO C12-ALKANEDIOLS AND TROPOLONE (DERIVATIVES)

(75) Inventors: Gerhard Schmaus, Höxter (DE); Sabine Lange, Holzminden (DE); Ravikumar Pillai, Emerson, NJ (US); William Johncock, Reinbek (DE)

(73) Assignee: Symrise AG, Holzminden (DE)

( * ) Notice: Subject to any disclaimer, the term of this patent is extended or adjusted under 35 U.S.C. 154(b) by 2109 days.

(21) Appl. No.: 11/460,587

(22) Filed: Jul. 27, 2006

(65) Prior Publication Data
US 2007/0059331 A1  Mar. 15, 2007

Related U.S. Application Data

(63) Continuation-in-part of application No. PCT/EP2006/050425, filed on Jan. 25, 2006.

(60) Provisional application No. 60/649,390, filed on Feb. 2, 2005.

(51) Int. Cl.
*A01N 31/02* (2006.01)
*A01N 35/06* (2006.01)

(52) U.S. Cl.
USPC ........... 424/405; 514/690; 514/738; 514/724; 514/675; 426/335; 424/44

(58) Field of Classification Search
USPC ................. 514/738, 724, 675, 690; 426/335; 424/44
See application file for complete search history.

(56) References Cited

U.S. PATENT DOCUMENTS

| 6,451,333 B1 * | 9/2002 | Beerse et al. ................. 424/405 |
| 6,554,620 B1 * | 4/2003 | Iwai .............................. 434/439 |

FOREIGN PATENT DOCUMENTS

| JP | 2001 278728 A | 3/2000 |
| JP | 2001 048781 A | 2/2001 |
| JP | 2002 212021 A | 7/2002 |
| JP | 2003 183113 A | 7/2003 |
| JP | 2005 162636 A2 | 12/2003 |
| JP | 2005 239965 A | 2/2004 |

OTHER PUBLICATIONS

RD 429093, 2000, Abstract from Derwent-ACC-2000-203857.*
Suzuki et al., Biochemical and Biophysical Research communication, vol. 275 (3), 2000, pp. 885-889.*
Abstract of Pillai, Ravi et al., "Cosmetic compositions containing mixtures of alkane diols and chelating agents, tropolone compounds and sesquiterpenes," Kenneth Mason Publications, Ltd., Research Disclosure (2005), 491 (Mar.), pp. 253-255, No. 491022.
Hori, Hitomi et al. (Feb. 21, 2001) "Use of hinokitiol an 1,2-alkanediol combination as antiseptic for topical preparations," XP002396727.
Pillai, Ravi et al. (Jul. 6, 2005) "Cosmetic compositions containing mixtures of alkane diols and chelating agents, tropolone compounds and sesquiterpenes," XP002396728.
Yatake, Masahiro (Sep. 8, 2005) "Aqueous ink compositions with antimicrobial ability," XP002396729.
Tachibana, Hisashi et al. (Jun. 23, 2005) "Deodorant compositions containing antibacterial glyceryl monoalkyl ethers," XP002396730.
Hisamitsu, Kazumasa et al. (Oct. 10, 2001) "Cosmetics containing tropolone derivatives and polyhydric alcohols," XP002396731.
Sakihara, Hisahiro et al. (Jul. 3, 2003) "Storage-stable antiseptic topical compositions," XP002396732.
Suetsugu, Kazuhiro et al. (Aug. 1, 2002) "Antibacterial cosmetic ingredients with moisture-holding effects," XP002396733.

* cited by examiner

*Primary Examiner* — Savitha Rao
(74) *Attorney, Agent, or Firm* — Duane Morris LLP; J. Rodman Steele, Jr.; Gregory M. Lefkowitz

(57) ABSTRACT

Antimicrobial mixtures comprising or consisting of:
one or more branched or unbranched alkanediols having 6-12 carbon atoms,
one, two or more compounds chosen from the group consisting of the tropolones of the formula (I)

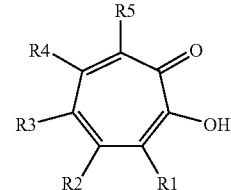

wherein the substituents R1, R2, R3, R4 and R5 independently of one another have the following meaning:
H;
linear or branched, saturated or unsaturated, aliphatic hydrocarbon radical having up to 30 C atoms;
OH;
OR6, wherein R6 is a linear or branched, saturated or unsaturated, aliphatic hydrocarbon radical having up to 30 C atoms;
COOH;
COOR7, wherein R7 is a linear or branched, saturated or unsaturated, aliphatic hydrocarbon radical having up to 30 C atoms;
$NO_2$;
$NH_2$;
F, Cl, Br, I;
are described.

18 Claims, No Drawings

SYNERGISTIC MIXTURES OF C6- TO C12-ALKANEDIOLS AND TROPOLONE (DERIVATIVES)

CROSS REFERENCE TO RELATED APPLICATIONS

This application is a continuation-in-part of co-pending PCT/EP2006/050425, filed on Jan. 21, 2006, and based upon U.S. Ser. No. 60/649,390 filed on Feb. 2, 2005 under the International Convention.

FIELD OF THE INVENTION

The present invention relates to the field of antimicrobial active compounds, and in particular certain mixtures, formulations and foodstuffs comprising at least one C6- to C12-alkanediol and at least one tropolone of the general formula (I) and to products comprising such mixtures in an antimicrobially active amount.

RELATED ART OF THE INVENTION

In the cosmetics and pharmaceutical and in the foodstuffs industry there is a constant need for agents having antimicrobial properties, in particular for the preservation of products which are otherwise perishable (such as e.g. cosmetics, pharmaceutical products or foodstuffs), but also for direct cosmetic or therapeutic treatment of microorganisms which can have an adverse influence on the human or animal body. Reference may be made by way of example to microorganisms which can cause body odour, acne, mycoses or the like.

In the technical fields referred to a large number of antimicrobial active compounds are indeed already employed, but alternatives nevertheless continue to be sought, in order to be able to perform targeted specific treatments and/or reduce side effects. In this context, however, in the search for alternative agents having an antimicrobial and in particular preserving action it is to be noted that the substances used in the cosmetics, pharmaceutical and/or foodstuffs field must be
- toxicologically acceptable,
- readily tolerated by the skin,
- stable (in particular in the conventional cosmetic and/or pharmaceutical formulations),
- largely and preferably completely odourless and
- inexpensive to prepare (i.e. employing standard processes and/or starting from standard precursors).

The search for suitable (active) substances which have one or more of the properties mentioned to an adequate extent is made difficult for the person skilled in the art in that there is no clear dependency between the chemical structure of a substance on the one hand and its biological activity against certain microorganisms (germs) and its stability on the other hand. Furthermore, there is no predictable connection between the antimicrobial action, the toxicological acceptability, the skin tolerability and the stability of a substance.

SUMMARY OF THE INVENTION

According to a first aspect, the invention relates to an antimicrobial mixture comprising or consisting of:
(a) one or more branched or unbranched alkanediols having 6-12 carbon atoms,
preferably one or more branched or unbranched 1,2-alkanediols having 6-12 carbon atoms,
and particularly preferably 1,2-hexanediol,
1,2-octanediol or
1,2-decanediol or
a mixture of 1,2-hexanediol and 1,2-octanediol or
a mixture of 1,2-hexanediol and 1,2-decanediol or
a mixture of 1,2-octanediol and 1,2-decanediol or
a mixture of 1,2-hexanediol, 1,2-octanediol and 1,2-decanediol,
(b) one, two or more compounds chosen from the group consisting of the tropolones of the formula (I)

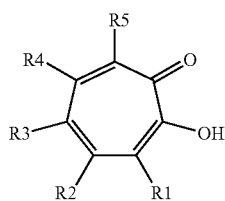

(c)

wherein the substituents R1, R2, R3, R4 and R5 independently of one another have the following meaning:

H;

linear or branched, saturated or unsaturated, aliphatic hydrocarbon radical having up to 30 C atoms;

OH;

OR6, wherein R6 is a linear or branched, saturated or unsaturated, aliphatic hydrocarbon radical having up to 30 C atoms;

COOH;

COOR7, wherein R7 is a linear or branched, saturated or unsaturated, aliphatic hydrocarbon radical having up to 30 C atoms;

$NO_2$, $NH_2$,

F, Cl, Br, I.

The contents of the alkanediols and tropolones of the formula (I) in the mixture here are preferably adjusted such that their antimicrobial action is intensified synergistically.

Alternatively or in addition to the particularly preferred 1,2-alkanediols, it is also possible to employ 1,6-hexanediol, 2-methylpentane-2,4-diol, 2,5-hexanediol, 3,6-octanediol, 2-ethyl-1,3-hexanediol, 1,3-octanediol, 1,3-decanediol and mixtures thereof with very good success in or as constituent (a).

Compounds which are preferred for use as constituent (b) in antimicrobial mixtures according to the invention are:

tropolone (formula (I): R1, R2, R3, R4, R5=H), alpha-thujaplicin ((formula (I): R1=iso-propyl, R2, R3, R4, R5=H), beta-thujaplicin (formula (I): R2=iso-propyl, R1, R3, R4, R5=H)

gamma-thujaplicin (formula (I): R3=iso-propyl, R1, R2, R4, R5=H)

and mixtures of these compounds of the formula (I).

The structural formula of the compound tropolone (CAS No.: 533-75-5; 2,4,6-cycloheptatrien-1-one, 2-hydroxy), which is particularly preferred for use in a mixture according to the invention, is:

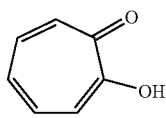

The invention is based on the surprising finding that the mixtures according to the invention show a synergistically intensified antimicrobial effect at least against selected germs, in particular against *Aspergillus niger*, a mould which can be combated only with great difficulty.

In particular, it has been found that the mixtures according to the invention can be used outstandingly as an antimicrobial active compound mixture, in particular for preserving otherwise perishable articles (see above).

Although persons skilled in the art have already addressed the antimicrobial properties of alkanediols and of tropolone and tropolone derivatives extensively, there has hitherto been no indication that the mixtures according to the invention of such compounds have a significantly improved antimicrobial action (at least against selected germs) in the individual case.

The antimicrobial action of tropolone and tropolone derivatives is known e.g. from Antimicrob. Agents Chemother. vol. 7(5), 500-506 (1975). However, studies of a synergistically intensified activity in combination with alkanediols against *Aspergillus niger* are not disclosed in any of these publications.

The antimicrobial action of polyols, in particular of aliphatic 1,2-diols and combinations of 1,2-diols with further antimicrobially active substances, is described in various documents. JP5191327, JP11322591, EP1206933 and WO 03/069994 may be mentioned here by way of example. However, studies of a synergistically intensified activity against *Aspergillus niger* in combination with tropolone or a tropolone derivative are not disclosed in any of these publications.

Polyols, and in particular 1,2-alkanediols, usually have only a deficient action against moulds such as *Aspergillus niger*. In respect of individual polyols or mixtures of polyols, a gap in the activity on moulds (e.g. the "problem germ" *Aspergillus niger*) is thus to be recorded. High use concentrations of individual polyols or of mixtures of polyols have therefore hitherto been necessary for complete inhibition of moulds.

JP2001278728 describes the use of tropolone derivatives in combination with polyols, such as dipropylene glycol, 1,3-butylene glycol and 1,2-pentanediol, in antimicrobial cosmetics. On the other hand, alkanediols having 6-12 carbon atoms are not described. A synergistic intensification in activity in the combination of a tropolone derivative with a branched or unbranched alkanediol having 6-12 carbon atoms is also not disclosed.

It was therefore particularly surprising that the mixtures according to the invention show a highly synergistic activity, and in the treatment of *Aspergillus niger* are significantly superior to
  individually dosed tropolones of the formula (I) and mixtures of tropolones of the formula (I) or
  individually dosed branched or unbranched alkanediols having 6-12 carbon atoms, in particular branched or unbranched 1,2-alkanediols having 6-12 carbon atoms, and chosen from this group in particular 1,2-hexanediol, 1,2-octanediol and 1,2-decanediol
  at the same concentration, in particular in respect of the reduction in germ count and the speed of the reduction in germ count. In particular, in the individual case a CFU value (CFU=number of colony-forming units) of 0 was achieved only with the said mixtures according to the invention.

On the basis of the particularly significant intensification in the action of their constituents, mixtures according to the invention are suitable in particular for combating *Aspergillus niger* even at a low dosage of the mixture according to the invention.

For the preparation of an effective mixture according to the invention which causes a complete reduction in the *Aspergillus niger* germ count, it is sufficient to mix one mixture constituent (a) comprising one or more branched or unbranched alkanediols having 6-12 carbon atoms, preferably at least one or more branched or unbranched 1,2-alkanediols having 6-12 carbon atoms, and from this group particularly preferably 1,2-hexanediol, 1,2-octanediol, 1,2-decanediol and mixtures thereof, with a small amount of constituent (b), i.e. one, two or more tropolones of the formula (I), for example an amount in the range of 0.001-10 wt. %, for example only 0.5-4 wt. %, based on the amount of constituent (a). If an amount of 0.3 wt. % 1,2-hexanediol and/or 1,2-octanediol and/or 1,2-decanediol is employed, this corresponds e.g. to an amount of tropolone(s) of just about 0.01 wt. %, in each case based on the total weight of the end product.

Based on the total weight of constituents (a) and (b) to be employed according to the invention, the content of constituent (a) is in the range of from 80 to 99.9 wt. %, but preferably in the range of 94-99 wt. %.

The antimicrobial mixtures according to the invention are suitable for preservation and antimicrobial treatment of perishable products, such as e.g. cosmetic products, pharmaceutical products or foodstuffs. In this context, the perishable product is brought into contact with an antimicrobially active amount, preferably an amount which is active against *Aspergillus niger*, of a mixture according to the invention. On the basis of their synergistically intensified antimicrobial activity, however, the mixtures according to the invention can also be employed
  for the cosmetic treatment of microorganisms which cause body odour,
  for the cosmetic treatment of microorganisms which cause acne,
  for the cosmetic treatment of microorganisms which cause mycoses and
  for the treatment of microorganisms on or in inanimate matter.

The mixtures according to the invention display their synergistically intensified antimicrobial action against a large number of Gram-positive bacteria, Gram-negative bacteria, moulds and yeasts. A particularly good action exists against Gram-negative bacteria, such as *Escherichia coli* and *Pseudomonas aeruginosa*, against yeasts, such as *Candida albicans* and precisely—as already mentioned—against fungi, such as *Aspergillus niger*. The very good activity of the mixtures according to the invention against *Aspergillus niger*, a mould which can be combated only with great difficulty, is to be regarded as particularly advantageous here.

The present invention also relates to the use of a mixture according to the invention, that is to say a mixture comprising or consisting of:
one or more branched or unbranched alkanediols having 6-12 carbon atoms, preferably one or more branched or unbranched 1,2-alkanediols having 6-12 carbon atoms, and chosen from this group particularly preferably 1,2-hexanediol, 1,2-octanediol and 1,2-decanediol
  one, two or more compounds chosen from the group consisting of tropolones of the formula (I), with the abovementioned meanings of the substituents, in particular the compounds described above as preferred, as an antimicrobial active compound mixture.

The present invention furthermore relates to corresponding methods for the cosmetic and/or therapeutic treatment of germs, and in particular especially of (a) microorganisms which cause body odour, (b) microorganisms which cause acne and/or (c) microorganisms which cause mycoses, comprising topical application of an antimicrobially active amount of a mixture according to the invention, the contents of the said diols in the mixture preferably being adjusted such that their antimicrobial action is synergistically intensified.

Preferred embodiments of the methods according to the invention correspond to the preferred embodiments of the use according to the invention which are explained above.

The human skin is populated by a large number of various microorganisms, which include the microorganisms already mentioned above, as well as others. Most of these microorganisms are not pathogenic and are irrelevant to the physiological state of the skin and to the odour thereof. On the other hand, others can influence the healthy state of the skin decisively.

As our own studies have now shown, the synergistically active mixtures according to the invention have a good action not only against the germs already named above, but also against *Staphylococcus epidermidis, Corynebacterium xerosis, Brevibacterium epidermidis, Propionibacterium* acnes and against *Trichophyton* and *Epidermophyton* species, so that they can also be employed as agents for the treatment of (combating) underarm and foot odour or body odour generally, as agents for combating acne, as antidandruff agents and for the treatment of mycoses (in particular dermatomycoses).

In the context of the present text, "treatment" is understood here as meaning any form of influencing of the microorganisms in question in which the multiplication of these microorganisms is inhibited and/or the microorganisms are killed.

The use concentration of a mixture according to the invention (which is preferably in a preferred embodiment) when used as a preservative or antimicrobial active compound in a foodstuff or a cosmetic or pharmaceutical formulation is preferably in the range of from 0.01 to 10 wt. %, but particularly preferably in the range of from 0.05 to 5 wt. %, in each case based on the total weight of the foodstuff or the formulation. The foodstuff and formulation additionally comprise conventional further constituents, in this context see below. The particular content of constituents (a) and/or (b) to be used according to the invention in mixtures according to the invention can be below the amount regarded as antimicrobially active in itself if the total amount of these substances which is present is sufficiently high to achieve an antimicrobial action of the total mixture. This applies in particular to the action against *Aspergillus niger*.

In a preferred method according to the invention for the cosmetic and/or therapeutic treatment of (a) microorganisms which cause body odour, (b) microorganisms which cause acne and/or (c) microorganisms which cause mycoses, the use concentration of the synergistically active mixtures according to the invention is also in the range between 0.01 and 10 wt. %, and particularly preferably in the range between 0.05 and 5 wt. %, in each case based on the total weight of the cosmetic or pharmaceutical product which comprises the mixture.

The synergistically active mixtures can be employed here (a) prophylactically or (b) as required.

The concentration of the amount of active compound to be applied e.g. daily varies and depends on the physiological state of the subject and individual-specific parameters, such as age or body weight. The synergistically active mixtures according to the invention can be employed either by themselves or in combination with further antimicrobially active substances.

In the context of the present text, it is to be pointed out that the 1,2-alkanediols to be employed according to the invention can be in the form of either the corresponding enantiomer of 2S configuration or the enantiomer of 2R configuration and in the form of any desired mixtures of these enantiomers of 2S and 2R configuration. For commercial reasons, it is indeed particularly advantageous to employ, for combating microorganisms, mixtures of racemates of the particular 1,2-alkanediols to be employed according to the invention, since these are particularly readily accessible by synthesis, but the pure enantiomers or non-racemic mixtures of these enantiomers are likewise suitable for the purposes according to the invention.

Further uses/methods and mixtures/compositions according to the invention can be found in the following statements and the attached patent claims.

Compositions which comprise a mixture according to the invention are, especially if they are employed against germs which cause body odour, as a rule applied topically in the form of solutions, creams, lotions, gels, sprays or the like. For other purposes, an oral (tablets, capsules, powders, drops), intravenous, intraocular, intraperitoneal or intramuscular administration or an administration in the form of an impregnated dressing is appropriate in some cases.

The mixtures according to the invention can be incorporated without difficulties into the usual cosmetic and/or dermatological formulations, such as, inter alia, pump sprays, aerosol sprays, creams, ointments, tinctures, lotions, nail care products (e.g. nail varnishes, nail varnish removers, nail balsams) and the like. It is also possible here, and in some cases advantageous, to combine the synergistic mixtures according to the invention with further active compounds, for example with other antimicrobially, antimycotically or antivirally active substances. The cosmetic and/or dermatological/keratological formulations comprising the synergistic mixtures according to the invention can otherwise have the conventional composition here and serve for the treatment of skin and/or hair in the sense of a dermatological treatment or a treatment in the sense of care cosmetics. However, they can also be employed in make-up products in decorative cosmetics.

If the mixtures according to the invention are employed as active compounds for preserving organic material, a further or several further preservatives can advantageously additionally be employed. Preservatives which are preferably chosen here are those such as benzoic acid, its esters and salts, propionic acid and its salts, salicylic acid and its salts, 2,4-hexadienoic acid (sorbic acid) and its salts, formaldehyde and paraformaldehyde, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylenediguanide) hydrochloride, 2-phenoxyethanol, hexamethylenetetramine, 1-(3-chloroallyl)-3,5,7-triaza-1-azonia-adamantane chloride, 1-(4-chlorophenoxy)-1-(1H-imidazol-1-yl)-3,3-dimethyl-2-butanone, 1,3-bis-(hydroxymethyl)-5,5-dimethyl-2,4-imidazolidinedione, benzyl alcohol, Octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3(2H)-isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$) trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidino-phenoxy)-n-hexane and its salts, glutaraldehyde, 5-ethyl-1-aza-3,7-dioxabicyclo(3.3.0) octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzyl-ammonium saccharinate, benzyl hemiformal, 3-iodo-2-propynyl butylcarbamate, sodium hydroxymethyl-aminoacetate or sodium hydroxymethylaminoacetate.

If the mixtures according to the invention are to be employed chiefly for inhibition of the growth of undesirable microorganisms on or in animal organisms, a combination with further antibacterial or antimycotic active substances is also advantageous here in some cases. In this respect, further active compounds which are worth mentioning, in addition to the large group of conventional antibiotics, are, in particular, the products relevant for cosmetics, such as triclosan, climbazole, octoxyglycerol, Octopirox (1-hydroxy-4-methyl-6-(2,4,4-trimethylpentyl)-2(1H)-pyridone, 2-aminoethanol), chitosan, farnesol, glycerol monolaurate or combinations of the substances mentioned, which are employed, inter alia, against underarm odour, foot odour or dandruff formation.

The mixtures according to the invention can advantageously be combined, in particular in cosmetic formulations, with further conventional constituents, such as, for example:

Further preservatives, further antimicrobial agents, such as e.g. further antibacterial agents or fungicides, abrasives, anti-acne agents, agents against ageing of the skin, anticellulitis agents, antidandruff agents, antiinflammatory agents, irritation-preventing agents, irritation-inhibiting agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substance, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxy-fatty acids, liquefiers, dyestuffs, colour-protecting agents, pigments, anticorrosives, aromas, flavouring substances, odoriferous substances, polyols, surfactants, electrolytes, organic solvents or silicone derivatives.

The mixtures according to the invention can moreover also particularly advantageously be employed in combination with perspiration-inhibiting active compounds (antiperspirants) for combating body odour. Perspiration-inhibiting active compounds which can be employed are, above all, aluminium salts, such as aluminium chloride, aluminium hydrochloride, nitrate, sulfate, acetate etc. In addition, however, the use of compounds of zinc, magnesium and zirconium may also be advantageous. For use in cosmetic and dermatological antiperspirants, the aluminium salts and—to a somewhat lesser extent—aluminium/zirconium salt combinations have essentially proved suitable. The aluminium hydroxychlorides which are partly neutralized and therefore tolerated better by the skin, but not quite so active, are additionally worth mentioning.

If the mixtures according to the invention are to be employed for antimicrobial treatment of a surface (e.g. of a human or animal body), a combination with (metal) chelators is advantageous in some cases. (Metal) chelators which are preferably to be employed here are, inter alia, α-hydroxy fatty acids, phytic acid, lactoferrin, α-hydroxy acids, such as, inter alia, citric acid, lactic acid and malic acid, and humic acids, bile acids, bile extracts, bilirubin, biliverdin or EDTA, EGTA and derivatives thereof.

It is moreover to be mentioned that the tropolones of the formula (I), in particular tropolone and the abovementioned thujaplicins, are (metal) chelators and are also very particularly suitable in this respect for use in cosmetic and dermatological formulations.

For use, the cosmetic and/or dermatologically active mixtures according to the invention are applied to the skin and/or hair in a sufficient amount in the conventional manner for cosmetics and dermatics. In this context, cosmetic and dermatological formulations which comprise a mixture according to the invention and additionally act as sunscreen compositions offer particular advantages. These formulations advantageously comprise at least one UVA filter and/or at least one UVB filter and/or at least one inorganic pigment. In this context, the formulations can be in various forms such as are conventionally employed e.g. for sunscreen formulations. They can be e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

As mentioned, formulations which comprise a mixture according to the invention can advantageously be combined with substances which absorb UV radiation, the total amount of the filter substances being e.g. 0.01 wt. % to 40 wt. %, preferably 0.1% to 10 wt. %, in particular 1.0 to 5.0 wt. %, based on the total weight of the formulations, in order to provide cosmetic formulations which protect the hair or skin from ultraviolet radiation.

It is known in the art that preserving aqueous sunscreen formulations containing a relatively high amount of organic UV filters (and mostly a relatively high sun protection factor (SPF), typically a SPF of about 15 and higher) is very difficult, especially against yeasts, in particular *Candida* yeasts (cf. U.S. Pat. No. 5,292,529). Hitherto it is not quite understood why such sunscreen formulations have these preserving problems.

It has now been found that the mixtures according to the invention, in particular mixtures comprising tropolone, preferably in combination with 1,2-hexanediol and 1,2-octanediol, have an excellent antimicrobial activity against yeasts, in particular against *Candida albicans*.

Preferred sunscreen formulations according to the present invention are aqueous emulsions, preferably of the water-in-oil (W/O) or of the oil-in-water (O/W) type or a multiple emulsion, for example of the water-in-oil-in-water (W/O/W) type, more preferably of the oil-in-water (O/W) type.

Preferred sunscreen formulations according to the present invention comprise a total amount of organic UV filters of greater than 10 wt. %, preferably in the range of from 12 to 40 wt. %, more preferred in the range of from 15 to 35 wt. %, based on the total weight of the sunscreen formulation.

In this context advantageous organic UV filters are:
p-aminobenzoic acid
p-aminobenzoic acid ethyl ester (25 mol) ethoxylated
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-ethylhexyl-2-cyano-3,3-diphenyl acrylate (Neo Heliopan®303)
ethyl-2-cyano-3,3'-diphenyl acrylate
2-phenylbenzimidazole sulfonic acid and salts (Neo Heliopan®Hydro)
3-(4'-trimethylammonium)benzylidene bornan-2-one methyl sulfate
terephthalylidene dibomane sulfonic acid and salts (Mexoryl®SX)
4-t-butyl-4'-methoxydibenzoyl methane (avobenzone)/ (Neoeliopan®357)
β-imidazole-4(5)-acrylic acid (urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
3-(4'-sulfo)benzylidene bornan-2-one and salts
3-(4'-methyl benzylidene)-d,l-camphor (Neo Heliopano®MBC)
3-benzylidene-d,l-camphor
4-isopropyl dibenzoyl methane
2,4,6-trianilino-(p-carbo-2'-ethylhexyl-1'-oxy)-1,3,5-triazine
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
N-[(2 and 4)-[2-(oxobom-3-ylidene) methyl]benzyl]acrylamide polymer
phenol, -(2H-benzotriazol-2-yl)-4-methyl-6-(2-methyl-3 (1,3,3,3-tetramethyl-1-(trimethylsilyl)oxy)disiloxyanyl)propyl), (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb®HEB)
2,2'-methylene bis-(6-(2H-benzotriazol-2-yl)-4-1,1,3,3-tetramethylbutyl)phenol), (Tinosorb®M)
2,4-bis-[4-(2-ethylhexyloxy)-2-hydroxyphenyl]-1,3,5-triazine
benzylidene malonate polysiloxane (Parsol®SLX)
glyceryl ethylhexanoate dimethoxycinnamate
disodium-2,2'-dihydroxy-4,4'-dimethoxy-5,5'-disulfobenzophenone
dipropylene glycol salicylate
sodium hydroxymethoxybenzophenone sulfonate
4,4',4-(1,3,5-triazine-2,4,6-triyltriimino)-tris-benzoic acid tris(2-ethylhexyl ester) (Uvinul®T150)
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3'5',5',5'-heptamethylsiloxy-2"-methylpropyloxy)-2-hydroxy}phenyl]-6-(4-methoxyphenyl)-1,3,5-triazine
2-(4-diethylamino-2-hydroxybenzoyl) benzoic acid hexyl ester (Uvinul® A Plus)
indanylidene compounds in accordance with DE 100 55 940 (=WO 02/38537)

Organic UV filters which are particularly preferred in a sunscreen formulation of the present invention, preferably in an above mentioned (preferred) amount, are:
p-aminobenzoic acid
3-(4'-trimethylammonium)benzylidene boman-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxobom-3-ylidene) methyl]benzyl]acrylamide polymer
p-methoxycinnamic acid-2-ethylhexyl ester (Neo Heliopan®AV)
p-aminobenzoic acid ethyl ester (25 mol) ethoxylated p-methoxycinnamic acid isoamyl ester (Neo Heliopan®E1000)

2,4,6-trianilino-(p-carbo-2'-ethylhexyl-1'-oxy)-1,3,5-triazine (Uvinul®T150)

phenol, 2-(2H-benzotriazol-2-yl)-4-methyl-6-(2-methyl-3 (1,3,3,3-tetramethyl-1-(trimethylsilyl)oxy)disiloxyanyl) propyl), (Mexoryl®XL)

4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)

3-(4'-methyl benzylidene)-d,l-camphor (Neo Heliopan®MBC)

3-benzylidene camphor salicylic acid-2-ethylhexyl ester (Neo Heliopan®OS)

4-dimethylaminobenzoic acid -2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl)phenol) (Tinosorb®M)

phenylene bis-benzimidazyl tetrasulfonic acid disodium salt (Neo Heliopan®AP)

2,4-bis-[{(4-(2-ethylhexyloxy)-2-hydroxy}phenyl]-6-(4-methoxyphenyl)-1,3,5-triazine, (Tinosorb®S)

benzylidene malonate polysiloxane (Parsol®SLX)

menthyl anthranilate (Neo Heliopan®MA)

2-(4-diethylamino-2-hydroxybenzoyl) benzoic acid hexyl ester (Uvinul® A Plus)

indanylidene compounds in accordance with DE 100 55 940 (=WO 02/38537)

Preferred sunscreen formulations according to the present invention have a SPF (sun protection factor) of equal or greater than 15, preferably of equal or greater than 20, more preferably of equal or greater than 30.

Preferred sunscreen formulations according to the present invention comprise 4-(1,1-dimethylethyl)-4'-methoxydibenzoylmethane (4-t-butyl-4'-methoxydibenzoyl methane; avobenzone), preferably in an amount in the range of from 0.2-10 wt. %, more preferred in the range of from 0.5-5 wt. %, based on the total weight of the sunscreen formulation.

In preferred sunscreen formulations according to the present invention the pH-value is in the range of from pH 4 to pH 8, preferably in the range of from pH 4.5 to pH 6.5.

A high content of care substances is regularly advantageous in formulations for topical prophylactic or cosmetic treatment of the skin comprising mixtures according to the invention. According to a preferred embodiment, the compositions comprise one or more animal and/or plant fats and oils having care properties, such as olive oil, sunflower oil, refined soya oil, palm oil, sesame oil, rapeseed oil, almond oil, borage oil, evening primrose oil, coconut oil, shea butter, jojoba oil, sperm oil, beef tallow, neat's foot oil and lard, and optionally further care constituents, such as, for example, fatty alcohols having 8-30 C atoms.

Care substances which can be combined in an outstanding manner with the synergistic mixtures according to the invention moreover also include ceramides, where ceramides are understood as meaning N-acylsphingosins (fatty acid amides of sphingosin) or synthetic analogues of such lipids (so-called pseudoceramides), which significantly improve the water retention capacity of the stratum corneum.

phospholipids, for example soya lecithin, egg lecithin and cephalins vaseline, paraffin oils and silicone oils; the latter include, inter alia, dialkyl- and alkylarylsiloxanes, such as dimethylpolysiloxane and methylphenylpolysiloxane, as well as alkoxylated and quaternized derivatives thereof.

Cosmetic formulations which comprise mixtures according to the invention can also comprise antioxidants, it being possible for all the antioxidants which are suitable or usual for cosmetic and/or dermatological uses to be used.

Cosmetic formulations which comprise mixtures according to the invention can also comprise vitamins and vitamin precursors, it being possible for all the vitamins and vitamin precursors which are suitable or usual for cosmetic and/or dermatological uses to be used. There are worth mentioning here, in particular, vitamins and vitamin precursors such as tocopherols, vitamin A, niacic acid and niacinamide, further vitamins of the B complex, in particular biotin, and vitamin C and panthenol and derivatives thereof, in particular the esters and ethers of panthenol and cationically derivatized panthenols, such as e.g. panthenol triacetate, panthenol monoethyl ether and the monoacetate thereof and cationic panthenol derivatives.

Cosmetic formulations which comprise mixtures according to the invention can also comprise antiinflammatory or redness- or itching-alleviating active compounds. All the antiinflammatory or redness- and itching-alleviating active compounds which are suitable or usual for cosmetic and/or dermatological uses can be used here.

Cosmetic formulations which comprise mixtures according to the invention can also comprise active compounds having a skin-lightening or skin-tanning action. According to the invention, all the skin-lightening or skin-tanning active compounds which are suitable or usual for cosmetic and/or dermatological uses can be used here.

Cosmetic formulations which comprise mixtures according to the invention can also comprise anionic, cationic, nonionic and/or amphoteric surfactants, especially if crystalline or microcrystalline solids, for example inorganic micropigments, are to be incorporated into the formulations.

The invention is explained in more detail in the following with the aid of an example. Unless stated otherwise, the data relate to the weight.

EXAMPLE 1

Comparison of Adequate Preservation of Cosmetic Formulations Comprising a Mixture of 1,2-hexanediol and 1,2-octanediol (Product A, not According To the Invention), Tropolone (Product B, not According to the Invention) and a Mixture of 1,2-hexanediol, 1,2-octanediol and tropolone (Product C, According to the Invention)

Testing for adequate preservation was carried out in accordance with the European Pharmacopoeia.

Testing thus comprises contamination of the formulation, if possible in its final condition, with a prescribed inoculum of suitable microorganisms, storage of the inoculated formulation at a certain temperature, removal of samples from the container at certain intervals of time and determination of the number of microorganisms in the samples removed in this way. The preserving properties are adequate if, under the conditions of the test, a clear reduction or, where appropriate, no increase in the germ count results in the inoculated formulations after the prescribed times at the prescribed temperatures. Experimental details of the test procedure are described in the European Pharmacopoeia (ISBN 3-7692-2768-9; Supplement 2001 to the 3rd Edition, page 421-422, chapter 5.1.3).

Test Germs:

The following microorganism strains were used for the tests for adequate preservation:

A: *Escherichia coli* ATCC 8739
B: *Pseudomonas aeruginosa* ATCC 9027
C: *Staphylococcus aureus* ATCC 6538
D: *Candida albicans* ATCC 10231
E: *Aspergillus niger* ATCC 16404

The initial germ count (CFU/g; "0 value") was in the range of from 250,000 to 320,000 in the various test series.

Formulation:

For the tests for adequate preservation, a defined amount of the active compound combination according to the invention (product C) was incorporated into an O/W emulsion. For comparison purposes, the comparison products (product A and B) were incorporated into separate O/W emulsions.

Formulations with products A, B and C:

TABLE 1

|  | INCI name | Manufacturer | Wt. % with "A" | Wt. % with "B" | Wt. % with "C" |
| --- | --- | --- | --- | --- | --- |
| Phase A | | | | | |
| Dracorin CE 614035 | Glyceryl Stearate Citrate | Symrise | 4.0 | 4.0 | 4.0 |
| PCL Solid 660086 | Stearyl Heptanoate, Stearyl Caprylate | Symrise | 3.0 | 3.0 | 3.0 |
| Paraffin oil °E | Paraffinum Liquidum | Parafluid | 7.0 | 7.0 | 7.0 |
| Lanette 18 | Stearyl Alcohol | Cognis | 1.5 | 1.5 | 1.5 |
| Dracorin GMS 647834 | Glyceryl Stearate | Symrise | 1.5 | 1.5 | 1.5 |
| Dow Corning 200 fluid | Dimethicone | Dow Corning | 2.0 | 2.0 | 2.0 |
| Phase B | | | | | |
| Water, demineralized | Water (Aqua) | | to 100 | to 100 | to 100 |
| Carbopol ETD 2050 Polymer | Carbomer | Noveon | 0.15 | 0.15 | 0.15 |
| 1,2-Hexanediol | 1,2-Hexanediol | Symrise | 0.25 | — | 0.15 |
| Caprylyl Glycol | Caprylyl Glycol | Symrise | 0.25 | — | 0.15 |
| Tropolone | | Symrise | — | 0.01 | 0.01 |
| Phase C | | | | | |
| Neutralizer AMP-95 | Amino Methylpropanol | Dow/Angus | 0.1 | 0.1 | 0.1 |
| Total: | | | 100.0 | 100.0 | 100.0 | pH: 5.5

Result:

The results of the preservative stress tests for *Aspergillus niger* for the active compound combinations investigated, comprising the mixture according to the invention (product C) or the comparison systems (products A and B) are compared in Table 2. The synergistic effect of the mixture according to the invention (product C) manifests itself here above all in the residual germ counts for *Aspergillus niger* which remain after 28 days. As can be seen from the table, it was possible to reduce the germ count of *Aspergillus niger*, a germ which is particularly problematic in respect of preservation of industrial products, to 0 within 28 days by using the mixture according to the invention. In contrast, the active compound tested in product A in a dosage of 0.5 wt. % for comparison purposes (1,2-hexanediol+1,2-octanediol; amounts ratio 1:1; w/w) rendered possible no such significant reduction in the number of colony-forming units (CFU), which also applies to product B (tropolone). This test series thus shows by way of example that active compound mixtures according to the invention have an action which is improved again synergistically compared with product A (mixture comprising 1,2-hexanediol and 1,2-octanediol; ratio of amounts 1:1; w/w).

Outstanding results which confirm the superiority of product C according to the invention were likewise obtained in respect of the further test germs.

TABLE 2

Testing for adequate preservation for product A, an active compound combination comprising 1,2-hexanediol and 1,2-octanediol in the amounts ratio of 1:1 (w/w), for product B (tropolone, formula (I): R1-R5 = H) and for product C, the mixture according to the invention comprising 1,2-hexanediol, 1,2-octanediol and tropolone

| Days | 0.5% product A (1,2-hexanediol plus 1,2-octanediol; 1:1 w/w) *Aspergillus niger* [CFU/ml] | 0.01% product B (tropolone) *Aspergillus niger* [CFU/ml] | 0.31% product C (0.3% 1,2-hexanediol plus 1,2-octanediol; 1:1 w/w and 0.01% tropolone) *Aspergillus niger* [CFU/ml] |
|---|---|---|---|
| 0 | 280,000 | 280,000 | 280,000 |
| 2 | 80,000 | 72,000 | 300 |
| 7 | 68,000 | 2,000 | 0 |
| 14 | 40,000 | 4,800 | 0 |
| 28 | 30,000 | 100 | 0 |

EXAMPLE 2

Comparison of Adequate Preservation of Cosmetic Formulations with a High Amount of Organic UV Filters and Having a SPF of Equal or Greater than 15

Testing for Adequate Preservation Against Germs in Sunscreen Formulations:

For the tests for adequate preservation, 1 wt. % of the respective active compound were incorporated into separate O/W emulsions: A2 is a comparison formulation and formulation C2 is according to the present invention.

TABLE 3

| Trade Name | INCI | A2 | C2 |
|---|---|---|---|
| Emulsiphos | Potassium cetyl phosphate, hydrogenated palm glycerides | 2.00 | 2.00 |
| PCL Solid | Stearyl heptanoate, stearyl caprylate | 2.00 | 2.00 |
| Lanette 16 | Cetyl alcohol | 1.50 | 1.50 |
| Dragoxat 89 | Ethylhexyl ethylisononanoate | 2.00 | 2.00 |
| Neutral Oil | Caprylic/capric triglyceride | 3.00 | 3.00 |
| Tegosoft TN | C12-15 Alkyl benzoate | 3.00 | 3.00 |
| Neo Heliopan BB | Benzophenone-3 | 6.00 | 6.00 |
| Neo Heliopan HMS | Homosalate | 10.00 | 10.00 |
| Neo Heliopan OS | Ethylhexyl salicylate | 5.00 | 5.00 |
| Neo Heliopan 357 | Butyl methoxy dibenzoylmethane | 3.00 | 3.00 |
| Neo Heliopan AV | Ethylhexyl methoxycinnamate | 7.50 | 7.50 |
| Carbopol ETD 2050 | Carbomer | 0.20 | 0.20 |
| Keltrol T | Xanthan gum | 0.20 | 0.20 |
| Water | Water (Aqua) | 50.45 | 50.45 |
| AMP | 2-Amino-2-methyl-1-propanol | 0.15 | 0.15 |
| Phenonip ® | Phenoxyethanol (and) Methylparaben (and) Butylparaben (and) Ethylparaben (and) Propylparaben | 1.00 | — |
| S68T | | — | 1.00 |

Phenonip® (not according to the present invention) is a commercially available (Clariant, Nipa preservatives) and in cosmetic formulations widely used antimicrobial active mixture consisting of phenoxyethanol, methylparaben, ethylparaben, butylparaben, propylparaben and isobutylparaben.

S68T is a mixture according to the present invention consisting of 49.5 wt. % 1,2-hexanediol, 49.5 wt. % 1,2-octanediol and 1 wt. % tropolone.

Testing for adequate preservation was carried out in accordance with the European Pharmacopoeia.

Testing thus comprises contamination of the formulation, if possible in its final condition, with a prescribed inoculum of suitable microorganisms, storage of the inoculated formulation at a certain temperature, removal of samples from the container at certain intervals of time and determination of the number of microorganisms in the samples removed in this way. The preserving properties are adequate if, under the conditions of the test, a clear reduction or, where appropriate, no increase in the germ count results in the inoculated formulations after the prescribed times at the prescribed temperatures. Experimental details of the test procedure are described in the European Pharmacopoeia (ISBN 3-7692-2768-9; Supplement 2001 to the 3rd Edition, page 421-422, chapter 5.1.3).

The initial germ count (CFU/g; "0 value") was in the range of from 230,000 to 400,000 in the various test series.

The following two antimicrobial active products were compared in view of their activity and efficacy with respect the above mentioned test germs:

Test Germs:

| Preservation test for *Escherichia coli* using strain *Escherichia coli* ATCC 8739 | | |
|---|---|---|
| days | A2 (Phenonip ®) | C2 (S68T) |
| 0 | 400,000 | 400,000 |
| 2 | 167000 | 0 |
| 7 | 26000 | 0 |
| 14 | 2100 | 0 |

Preservation test for *Pseudomonas aeruginosa* using strain *Pseudomonas aeruginosa* ATCC 9027

| days | A2 (Phenonip ®) | C2 (S68T) |
|---|---|---|
| 0 | 230,000 | 230,000 |
| 2 | 0 | 0 |
| 7 | 0 | 0 |
| 14 | 0 | 0 |

Preservation test for *Staphylococcus aureus* using strain *Staphylococcus aureus* ATCC 6538

| days | A2 (Phenonip ®) | C2 (S68T) |
|---|---|---|
| 0 | 300,000 | 300,000 |
| 2 | 32000 | 0 |
| 7 | 900 | 0 |
| 14 | 100 | 0 |

Preservation test for *Candida albicans* using strain *Candida albicans* ATCC 10231

| days | A2 (Phenonip ®) | C2 (S68T) |
|---|---|---|
| 0 | 400,000 | 400,000 |
| 2 | 194,000 | 120,000 |
| 7 | 157,000 | 100 |
| 14 | 157,000 | 0 |

Preservation test for *Aspergillus niger* using strain *Aspergillus niger* ATCC 16404

| days | A2 (Phenonip ®) | C2 (S68T) |
|---|---|---|
| 0 | 230,000 | 230,000 |
| 2 | 189,000 | 40,000 |
| 7 | 93,000 | 500 |
| 14 | 3,000 | 0 |

Formulation F1: Sunscreen lotion

| Raw Material | % weight |
|---|---|
| Phase 1 | |
| Potassium Cetyl Phosphate, Hydrogenated Palm Glycerides | 1.00 |
| alpha-Bisabolol | 0.10 |
| Cetearyl Alcohol | 1.50 |
| Myristyl Myristate | 1.00 |
| etearyl Ethylhexanoate | 4.00 |
| Stearyl Heptanoate, Stearyl Caprylate | 1.00 |
| Cyclopentasiloxane, Cyclohexasiloxane | 0.50 |
| Butyl Methoxydibenzoylmethane (avobenzone) | 1.50 |
| 4-Methylbenzylidene Camphor | 1.50 |
| Ethylhexyl Methoxycinnamate (Neo Heliopan ®AV) | 8.00 |
| VP/Hexadecene Copolymer | 1.00 |

Formulation F1: Sunscreen lotion (continued)

| Raw Material | % weight |
|---|---|
| Acrylates/C 10-30 Alkyl Acrylate Crosspolymer | 0.10 |
| Phase 2 | |
| Water | Ad 100 |
| Pentylene Glycol (1,2-Pentanediol) | 2.00 |
| Caprylyl Glycol (1,2-Octanediol) | 0.80 |
| Phase 3 | |
| Sodium Hydroxide, 10% solution | — |
| Phase 4 | |
| Fragrance | 0.20 |
| Phase 5 | |
| Tropolone | 0.02 |

Formulation F2: Silicone Emulsion

| Raw Material | % weight |
|---|---|
| Phase 1 | |
| Potassium Cetyl Phosphate, Hydrogenated Palm Glycerides | 1.00 |
| Cyclohexasiloxane | 4.00 |
| Cetearyl Alcohol | 1.50 |
| Phenyl Trimethicone | 3.00 |
| Stearyl Heptanoate, Stearyl Caprylate | 3.00 |
| Dimethicone | 1.00 |
| Xanthan Gum | 0.20 |
| Isoamyl p-Methoxycinnamate | 5.00 |
| p-methoxycinnamic acid-2-ethylhexyl ester (Neo Heliopan ®AV) | 5.00 |
| Butyl Methoxydibenzoylmethane (avobenzone) | 0.50 |
| Phase 2 | |
| Water | Ad 100 |
| 1,2-Hexanediol | 0.40 |
| Caprylyl Glycol (1,2-Octanediol) | 0.60 |
| Phase 3 | |
| Tropolone | — |

Formulation F3: W/O sunscreen lotion

| Raw Material | % weight |
|---|---|
| Phase 1 | |
| Polyglyceryl-2 Dipolyhydroxystearate | 3.00 |
| Glyceryl Oleate | 1.00 |
| Beeswax | 1.20 |
| Ethylhexyl Isononanoate | 2.00 |
| Caprylic/Capric Triglyceride | 3.00 |
| C 12-15 Alkyl Benzoate | 3.00 |
| Benzophenone-3 | 6.00 |
| Homosalate | 10.00 |
| Ethylhexyl Salicylate | 5.00 |
| Butyl Methoxydibenzoylmethane (avobenzone) | 3.00 |
| Ethylhexyl Methoxycinnamate | 7.50 |

-continued

| Formulation F3: W/O sunscreen lotion | |
|---|---|
| Raw Material | % weight |
| Phase 2 | |
| Water | Ad 100 |
| 1,2-Hexanediol | 0.25 |
| Caprylyl Glycol (1,2-Octanediol) | 0.25 |
| Phase 3 | |
| Magnesium Sulfate | — |
| Phase 4 | |
| Sodium Chloride | 0.50 |
| Phase 5 | |
| Tropolone | 0.02 |

What is claimed:

1. Antimicrobial mixture comprising:
   (a) at least one branched or unbranched alkanediol having 6-12 carbon atoms, wherein constituent (a) comprises one or more unbranched 1,2-alkanediol having 6-12 carbon atoms, and
   (b) tropolone, formula (I)

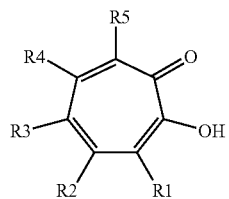

wherein the substituents R1, R2, R3, R4 and R5 are H, wherein a ratio of constituent (a) to constituent (b) ranges from 1:0.00001 to 1:0.1, and wherein said mixture exhibits synergistically enhanced antimicrobial properties relative to constituent (a) alone and relative to constituent (b) alone.

2. Antimicrobial mixture according to claim 1, wherein
1,2-hexanediol,
1,2-octanediol or
1,2-decanediol or
a mixture of 1,2-hexanediol and 1,2-octanediol or
a mixture of 1,2-hexanediol and 1,2-decanediol or
a mixture of 1,2-octanediol and 1,2-decanediol or
a mixture of 1,2-hexanediol, 1,2-octanediol and 1,2-decanediol is employed as constituent (a).

3. Cosmetic or pharmaceutical formulation or foodstuff comprising an antimicrobial mixture comprising or consisting of constituents (a) and (b) according to claim 1 and
   further conventional constituents
   the total amount of constituents (a) and (b) being in the range of from 0.01 to 10 wt. %, based on the total weight of the formulation or of the foodstuff, wherein said mixture exhibits synergistically enhanced antimicrobial properties relative to constituent (a) alone and relative to constituent (b) alone.

4. Antimicrobial mixture according to claim 1, wherein the amount of constituent (a) and/or the amount of constituent (b) in each case considered in itself is not antimicrobially active, but the total amount of constituents (a) and (b) is antimicrobially active.

5. Method for the preservation or antimicrobial treatment of a perishable product, with the following step:
   bringing of the perishable product into contact with an antimicrobially active amount, preferably an amount which is active against *Aspergillus niger*, of a mixture according to claim 1.

6. Method for the cosmetic and/or therapeutic treatment of
   (i) microorganisms which cause body odour,
   (ii) microorganisms which cause acne and/or
   (iii) microorganisms which cause mycoses,
   comprising topical application of an antimicrobially active amount of a mixture according to claim 1.

7. Cosmetic or pharmaceutical formulation or foodstuff according to claim 3, wherein the amount of constituent (a) and/or the amount of constituent (b) in each case considered in itself is not antimicrobially active, but the total amount of constituents (a) and (b) is antimicrobially active.

8. Cosmetic or pharmaceutical formulation or foodstuff according to claim 3, wherein said antimicrobial mixture exhibits synergistically enhanced antimicrobial properties against *Aspergillus niger* relative to constituent (a) alone and relative to constituent (b) alone.

9. Cosmetic or pharmaceutical formulation or foodstuff according to claim 3, wherein said cosmetic or pharmaceutical formulation or foodstuff is a foodstuff.

10. Antimicrobial mixture according to claim 1, wherein said antimicrobial mixture exhibits synergistically enhanced antimicrobial properties against *Aspergillus niger* relative to constituent (a) alone and relative to constituent (b) alone.

11. Antimicrobial mixture according to claim 7, wherein the total amount of constituents (a) and (b) is in the range of from 0.01 to 10 wt % based on the total weight of the mixture.

12. Antimicrobial mixture according to claim 1, wherein constituent (a) consists of at least one unbranched 1,2-alkanediol having 6-12 carbon atoms.

13. Antimicrobial mixture according to claim 12, wherein the total amount of constituents (a) and (b) is in the range of from 0.01 to 10 wt. %, based on the total weight of the mixture.

14. Antimicrobial mixture according to claim 12, wherein constituent (a) comprises a diol selected from the group consisting of 1,2-hexanediol, 1,2-octanediol, 1,2-decanediol and mixtures thereof.

15. Antimicrobial mixture according to claim 14, wherein the total amount of constituents (a) and (b) is in the range of from 0.01 to 10 wt. %, based on the total weight of the mixture.

16. Antimicrobial mixture according to claim 1, wherein constituent (a) comprises an alkanediol selected from the group consisting of 1,6-hexanediol, 2-methylpentane-2,4-diol, 2,5-hexanediol, 3,6-octanediol, 2-ethyl-1,3-hexanediol, 1,3-octanediol, 1,3-decanediol, and mixtures thereof.

17. Antimicrobial mixture according to claim 1, wherein constituent (a) comprises a 1,2-alkanediol selected from the group consisting of 1,2-hexanediol, 1,2-octanediol, 1,2-decanediol and mixtures thereof.

18. Antimicrobial mixture according to claim 17, wherein the total amount of constituents (a) and (b) is in the range of from 0.01 to 10 wt. %, based on the total weight of the mixture.

* * * * *